United States Patent
Ley et al.

(10) Patent No.: US 9,506,905 B2
(45) Date of Patent: Nov. 29, 2016

(54) SYSTEM AND METHOD FOR RAPID MEASUREMENT OF THE AIR VOID DISTRIBUTION OF FRESH CONCRETE

(71) Applicants: Matthew Tyler Ley, Stillwater, OK (US); Robert Mabrey Frazier, Tulsa, OK (US); Braden Michael Tabb, Tulsa, OK (US)

(72) Inventors: Matthew Tyler Ley, Stillwater, OK (US); Robert Mabrey Frazier, Tulsa, OK (US); Braden Michael Tabb, Tulsa, OK (US)

(73) Assignee: The Board of Regents for Oklahoma State University, Stillwater, OK (US)

(*) Notice: Subject to any disclaimer, the term of this patent is extended or adjusted under 35 U.S.C. 154(b) by 589 days.

(21) Appl. No.: 14/029,473

(22) Filed: Sep. 17, 2013

(65) Prior Publication Data
US 2014/0096593 A1    Apr. 10, 2014

Related U.S. Application Data

(60) Provisional application No. 61/701,761, filed on Sep. 17, 2012.

(51) Int. Cl.
*G01N 33/38* (2006.01)
*G01N 7/00* (2006.01)

(52) U.S. Cl.
CPC .............. *G01N 33/383* (2013.01); *G01N 7/00* (2013.01)

(58) Field of Classification Search
CPC .............................. G01N 33/383; G01N 7/00
USPC .................. 73/803, 78, 84, 784, 37, 38, 865
See application file for complete search history.

(56) References Cited

U.S. PATENT DOCUMENTS

| | | | | |
|---|---|---|---|---|
| 6,799,471 | B1* | 10/2004 | Regimand | G01N 3/36 137/386 |
| 2007/0186697 | A1* | 8/2007 | Sogo | B28C 7/0409 73/865 |
| 2010/0116030 | A1* | 5/2010 | Khan | G01N 15/08 73/38 |

FOREIGN PATENT DOCUMENTS

| | | |
|---|---|---|
| EP | 1043585 A2 | 10/2000 |
| JP | 2000-088843 | 3/2000 |
| JP | 2002-355811 | 12/2002 |

OTHER PUBLICATIONS

PCT/US2013/060184—International Search Report and Written Opinion.
ASTM Designation: C231/C231M—10 "Standard Test Method for Air Content of Freshly Mixed Concrete by the Pressure Method", published Nov. 2010, ASTM International, West Conshohocken, Pennsylvania.

* cited by examiner

*Primary Examiner* — Michael A Lyons
*Assistant Examiner* — Suman K Nath
(74) *Attorney, Agent, or Firm* — Fellers, Snider, Blankenship, Bailey & Tippens, P.C.; Terry L. Watt

(57) ABSTRACT

According to an embodiment, there is provided herein a method of determining the air void distribution in a sample of fresh concrete. One embodiment of the invention determines a parameter related to air void distribution by applying a known pressure to a fresh concrete sample, measuring a first value representative of the volume under compression, releases at least a portion of the pressure, reapplies the same pressure to the sample, measures a second value representative of the volume under the second compression, and uses differential between the first and second values to estimate a parameter related to the air void distribution.

16 Claims, 2 Drawing Sheets

SYSTEM AND METHOD FOR RAPID MEASUREMENT OF THE AIR VOID DISTRIBUTION OF FRESH CONCRETE

CROSS REFERENCE TO RELATED APPLICATIONS

This application claims the benefit of U.S. Provisional Patent Application Ser. No. 61/701,761 filed on Sep. 17, 2012 and incorporates said provisional application by reference into this document as if fully set out at this point.

STATEMENT REGARDING FEDERAL SPONSORED RESEARCH OR DEVELOPMENT

This invention was made with U.S. Government support under DOT Grant No. DTRT06-G-0016 awarded by the U.S. Department of Transportation. The Government has certain rights in this invention

TECHNICAL FIELD

This disclosure is related to the construction field and, more particularly, to systems and methods for determine the volume and size distribution of air in a fresh concrete mixture.

BACKGROUND

It is important to ensure that concrete is frost durable in environments where it might be subjected to moisture and subsequent freezing and thawing cycles. This is done by adding specialized surfactants that stabilize air while mixing concrete. The air voids allow space for water to move during freezing. The size distribution of the voids is very important to the frost durability of concrete. Currently, there are no testing methods that allow the spacing of these voids to be determined in the fresh concrete in less than 30 minutes. Instead, either a volume of air is specified or testing must be postponed until the concrete has hardened. With hardened concrete, it can be cut and then polished and the voids on the surface can be measured and counted with American Society for Testing and Materials ("ASTM") procedure C 457. This method aims to measure the air content, spacing factor, and specific surface of the concrete. This is a very time consuming and costly process.

Currently one test method exists to determine the size distribution of an air void system in fresh concrete. This proprietary test is called the Air Void Analyzer ("AVA"). This test involves injecting mortar collected from concrete into a thinning liquid that is being stirred. The air voids in the mortar are liberated and they slowly rise to the top of a column of water. A petri dish is attached to a scale or a strain gage at the top of the apparatus to measure the buoyancy force created by the air voids over time. From this data, various qualities such as the air content, spacing factor, and specific surface can be estimated.

The accuracy of this test has been called into question. It also takes more than 30 minutes to complete and the specialized testing device is very costly and cannot readily be used on a jobsite. The results are highly variable due to any number of factors, including: vibration, operator, sampling process, and time duration between sampling and testing.

Since the size of bubbles cannot currently be reliably measured in fresh concrete, it is common to use a test that instead measures the volume of air in concrete. There are three common tests that are able to do this. The most commonly used test is the ASTM C 231 pressure meter. This test is based on the observation that the only material that is readily compressible inside of confined concrete that has not hardened is the air voids. Since these pressures are low, the response is assumed to be linear and Boyle's Law can be used to estimate the volume of the air in the concrete. In brief, the associated method of testing involved connecting two chambers together. One chamber was initially left empty and the other was filled with the subject concrete of a known volume. Water was then added above the concrete to ensure the bottom chamber is filled. The top chamber of a known volume was then increased in pressure to about 14.5 psi. The top chamber was then opened into the bottom chamber to provide fluid communication and combined chambers were allowed to reach an equilibrium pressure. From this pressure, the total volume of air within the concrete can be estimated. As stated previously, this is the most widely used test method to determine the air content of the mixture. One problem with this approach is that it can only measure the volume of air and does not give information about the void size distribution.

Another commonly utilized test is the ASTM C 457 Hardened Air Void Analysis, which can be used to examine the air void system in hardened concrete. However, one problem with this sort of analysis is that results can take weeks to obtain. This makes it impossible to evaluate the acceptability of the freeze thaw durability before the concrete has been poured and hardened. The slow process that is hardened air void analysis is a cause for sluggish laboratory studies in which large data sets can be difficult and tedious to produce.

"Spacing factor" is a measure of half the average spacing between the average sized air void in the paste and is determined through investigation of the hardened concrete as described in ASTM C 457. Freeze thaw testing has shown that concrete with a spacing factor less than 0.008 in. is sufficient to resist frost damage and the American Concrete Institute 201 uses this value as one of its standards. Research has shown that different combinations of admixtures can have a significant impact on the size of the bubbles stabilized in concrete. Because of this, different volumes of air are required to achieve this critical spacing factor. However, it should be noted that these required air volumes can change with the temperature, mixing method, placement technique, and combination of other admixtures used. For example, if an air-entraining agent is used then about 3.5% air is required before satisfactory frost performance is achieved. If a polycarboxylate (PC) water reducer or dispersant is used with an AEA then a 7.5% air content may be necessary to achieve a spacing factor of 0.008 in.

Heretofore, as is well known in the concrete testing arts, there has been a need for a system and method of determining the air void size distribution in fresh concrete that is more cost effective and timelier than current methods. Accordingly, it should now be recognized, there exists, and has existed for some time, a very real need for a method of fresh concrete evaluation that would address and solve the above-described problems.

Before proceeding to a description of the present invention, however, it should be noted that the description of the invention which follows, together with the accompanying drawings, should not be construed as limiting the invention to the examples (or embodiments) shown and described. This is so because those skilled in the art to which the invention pertains will be able to devise other forms of this invention within the ambit of the appended claims.

SUMMARY

According to an embodiment, the instant inventors have invented a method to determine a parameter that corresponds to the distribution of the size of the air bubbles in a fresh concrete mixture, where "fresh concrete" should be understood to be concrete before it has initially set.

One goal of an embodiment is to determine a method for predicting the air void size distribution in fresh concrete. Previous research has shown that as the volume of air increases the average spacing between voids, or the spacing factor, will decrease. However, different mixtures decrease at different rates and therefore require different amounts of entrained air in the mixture to provide freeze thaw protection to the concrete.

An embodiment uses an observation that a fresh concrete mixture that is loaded and then subsequently unloaded and loaded again will not have the same load versus deformation or volume change curve. This difference in response correlates to the air void distribution or the spacing factor in fresh concrete. This method applies to one or a series of sequential external loads or pressures to the fresh concrete and then reapplies them again to the same material and compares the response.

A Super Air Meter ("SAM", hereinafter) device and associated method to measure the response of fresh concrete to a series of pressures increases is described herein. One embodiment of the method taught herein uses a device that is similar to the traditional ASTM C 231 pressure meter and, using such device, can accurately determine the air content in addition to the air void distribution in a fresh concrete sample.

By way of summary of one embodiment, the disclosed testing method operates as follows. Consolidated concrete of a known volume is placed in one chamber of a two chamber system (e.g., the bottom chamber), after which a fluid of known compressibility such as water is added until that chamber is full. Another chamber (e.g., the top chamber) is then pressurized to a first pressure. The two chambers are then placed into fluid communication with each other until an equilibrium pressure is reached. That pressure is then recorded. The two chambers are then removed from fluid communication with each other and pressure in the chamber containing the concrete is at least partially released.

Next and continuing with the current example, the chamber without the concrete is pressurized to a second pressure. The two chambers are again brought into fluid communication and such communication is maintained until the two chambers reach an equilibrium pressure. The resulting equilibrium pressure is recorded. According to this embodiment, this process can be repeated for additional pressures if desired. As is shown herein, the recorded equilibrium pressures, and especially their numerical differences, can be used to estimate the size distribution of compressible air space in the concrete sample.

In some embodiments, the same sample of concrete can then be retested in the same manner stated above. It is possible to run a third (or fourth, etc.) set of pressures to compare to the second if desired. However, that typically would not be necessary.

In still other embodiments and as is explained more fully below, the test could be conducted using only a single chamber. For example, a known volume of concrete could be subjected to an overpressure load, volumetrically measured, released, subjected to the same or a similar overpressure again and measured again. The differential volume would then be indicative of the air void distribution in the same way that the equilibrium pressure differentials are so indicative.

According to an embodiment, there is taught herein a method of determining a parameter indicative of an air void distribution of a fresh concrete sample, wherein is provided a first and a second container configurable to be placed into fluid communication with each other, the method comprising: placing said concrete sample in said first container; adding a fluid to said first container containing said concrete until it is substantially full; pressurizing said second container to a first pressure; placing said first container and said second container in fluid communication; determining a first equilibrium pressure; releasing at least a part of the pressure in the first container; removing said first and second container from fluid communication; pressurizing said second container to a second pressure; bringing said first container and said second container back into fluid communication with each other; determining a second equilibrium pressure; and, using at least said first equilibrium pressure and said second equilibrium pressure to determine said parameter indicative of said air void distribution of said concrete sample.

According to another embodiment, there is provided herein a method of determining a parameter representative of an air void distribution of a fresh concrete sample, the method comprising: subjecting said concrete sample to a first load; determining a first value representative of a first volume while said concrete sample is subject to said first load; releasing said concrete sample from at least a portion of said first load; subjecting said concrete sample to a second load; determining a second value representative of a second volume while said concrete sample is subject to said second load; and, using at least said first value representative of said first volume and said second value representative of said second volume to determine a parameter representative of said air void distribution of said concrete sample.

The foregoing has outlined in broad terms the more important features of the invention disclosed herein so that the detailed description that follows may be more clearly understood, and so that the contribution of the instant inventors to the art may be better appreciated. The instant invention is not limited in its application to the details of the construction and to the arrangements of the components set forth in the following description or illustrated in the drawings. Rather the invention is capable of other embodiments and of being practiced and carried out in various other ways not specifically enumerated herein. Additionally, the disclosure that follows is intended to apply to all alternatives, modifications and equivalents as may be included within the spirit and the scope of the invention as defined by the appended claims. Further, it should be understood that the phraseology and terminology employed herein are for the purpose of description and should not be regarded as limiting, unless the specification specifically so limits the invention.

DETAILED DESCRIPTION

Figure 1:
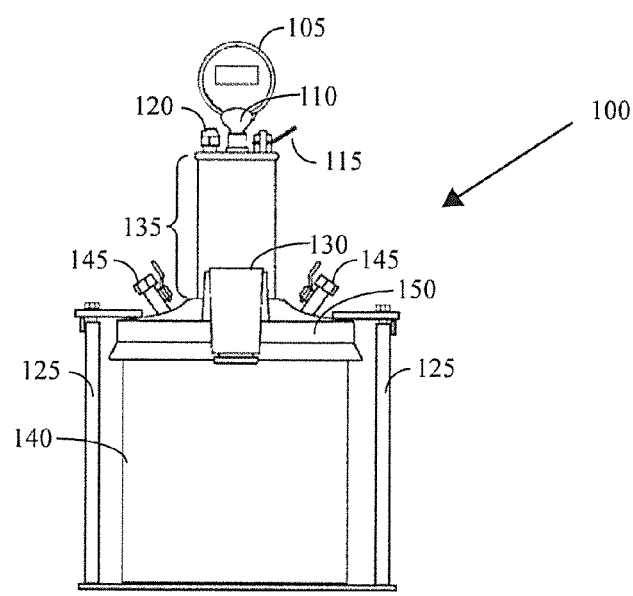
FIG. 1 contains a schematic illustration of an embodiment.

While this invention is susceptible of embodiment in many different forms, there is shown in the drawings, and will herein be described hereinafter in detail, some specific embodiments of the instant invention. It should be understood, however, that the present disclosure is to be considered an exemplification of the principles of the invention and is not intended to limit the invention to the specific embodiments or algorithms so described.

The instant disclosure is generally directed toward a procedure suitable for use in estimating air void size distribution that is generally based on the finding that different responses are obtained when fresh concrete is tested in a pressure/release/pressure can be related to the ASTM C 457 spacing factor. As discussed previously the spacing factor is commonly used to evaluate the suitability of concrete for exposure to freezing/thawing conditions.

Turning first to a discussion of a device suitable for use with the methods disclosed herein, according to an embodiment, there is provided a Super Air Meter ("SAM") device and associated method of testing that can be used to estimate the spacing factor of fresh concrete. Turning first to the example device 100 of FIG. 1, this figure illustrates some aspects of an embodiment of the SAM 100 testing apparatus as it might appear within a reinforcing cage 125. Note that, in some embodiments and at some pressures, the reinforcing cage 125 would not be necessary could be replaced by, for example, additional clamps 130 or completely different hardware that is specifically designed to accommodate the pressures utilized by this embodiment.

As can be seen, this embodiment comprises lower 140 and upper 135 chambers which are configurable to be placed in fluid communication with each other. A pressure gage 105 will be used to monitor the pressure within the upper chamber 135 and is a digital gage in some embodiments. It would be best if the gage 105 were accurate to the nearest 0.01 psi throughout its range. Because accurate pressure readings are generally desirable and can contribute to a more accurate calculations, a digital gage would often be preferred but this is not a requirement.

Air bleeder valve 120 has been provided to allow pressure within the chamber 135 to be reduced. Main air valve 115 is used to control the flow of pressurize air into the upper chamber 135. Clamp 130 (and additional clamps not shown) is provided to secure the upper 135 and lower 140 chambers together. Finally petcocks 145 are used in this embodiment as conduits for adding fluids such as water to this embodiment of the device 100.

In practice, according to one embodiment the fresh concrete that is to be tested is placed and consolidated in lower chamber 140, which in some embodiments will be a quarter cubic foot in volume as in ASTM C231, the disclosure of which is incorporated herein by reference as if fully set out at this point. The apparatus of this embodiment is similar to a ASTM C 231 Type B meter with a vertical air chamber 135 that is clamped to a lower chamber 140 that contains the concrete that is to be tested. However, in this embodiment the chamber should be one that is configured to at least tolerate internal pressures of 75 psi, if that is to be the top pressure used in testing. The cover of the upper chamber 135 should also include an air pressure gage 105 that has a range that is commensurate with the pressures that are to be used during testing, e.g., in this embodiment a range of about 0 to at least 75 psi would be useful.

According to an embodiment and as is summarized in Table 1 below, as an initial step some amount of consolidated concrete will be added to the bottom chamber 140 after which the lid 150 and upper chamber 135 on top of the bottom chamber 140 will be secured. Water is then added through the petcock valves 145 until the bottom chamber 140 is full. Note that, although water is a suitable material to add to the chamber 140, in fact any fluid might be used with a known compressibility. However, adding a fluid that is noncompressible to the bottom chamber 140 is not absolutely essential but such will tend to make the resulting measurements more reliable.

Continuing with the current example, the top chamber 135 is then pressurized to a first pressure, e.g., 14.5 psi, and allowed to stabilize for some period of time, e.g., 10 seconds. One advantage of this step is that it will let the compressed air in the top chamber cool to room temperature.

Further with respect to the current example, after the pressure has stabilized the top 135 and bottom 140 chambers are then brought into fluid communication with each other, e.g., by activating a lever or otherwise removing an air seal between the them. The pressure between the now-connected chambers 135 and 140 is allowed to equalize which might take up to 10 seconds in some embodiments, which depends on many different factors. During the pressure equalization phase, in this embodiment the bottom chamber 140 might be sharply struck with a rubber mallet (not shown) around its sides. However, that is not a requirement. It is important for this embodiment that the two chambers be maintained in fluid communication until the pressure in the top chamber 135 stops changing. In some instances it was found that 10 seconds was long enough for this to occur. This first equilibrium pressure is recorded.

Next, and without opening the petcocks or releasing air from the bottom chamber or top chamber, in an embodiment the top chamber 135 is pressurized to an initial pressure of 30 psi and allowed to stabilize. Again, the lever is pressed to allow the top chamber 135 and bottom chamber 140 to reach an equilibrium pressure. The resulting pressure is again recorded.

Continuing with this particular variation, the process is repeated for a top chamber 135 with a volume of 23 cubic inches with initial pressures of 45 psi±0.1 psi, 60 psi±0.1 psi, and 75 psi±0.1 psi. Note that, in some embodiments, the test might terminate after a single higher pressure episode which might be over 100 psi. However, in other embodiments multiple pressures lower or higher than those values will be utilized. For example, one embodiment of the invention involves three pressures of 14.5 psi, 30 psi, and 45 psi.

Continuing with the instant example, after the equilibrium pressure from the last pressure to be tested in this first run is recorded (e.g., 75 psi), the petcocks 145 will be opened and the lever is pressed to return all the pressures from the bottom chamber 140 and the top chamber 135 back to atmospheric pressure. That being said, all that would be required is to lessen the pressure in the lower chamber 140 by some amount so that the bubbles in the concrete be given an opportunity to expand, i.e., the pressure need not be returned to atmospheric pressure. However, for purposes of the instant example, it would be assumed that the pressure in the lower chamber 140 has been allowed to return to the ambient air pressure.

With respect to the foregoing, note that it is preferred as previously indicated that all pressure measurements taken herein be accurate to within ±0.01 psi. However, if such accuracy is not available the methods taught herein will still work but the accuracy of the estimate might suffer as a result.

In this embodiment the period during which fluid communication between the chambers is maintained should be about 10 seconds to allow the pressures to equalize. Of course, that time is only given as an example and depends on a number of factors which those of ordinary skill in the art will readily recognize. During which time in which the pressures are equalizing, it is useful in some embodiment to smartly strike the bottom chamber 140 with a rubber mallet around its periphery, in some cases 10 or so hits would suffice.

In some embodiments, the same sample of concrete might be tested again in the manner set out above in order to confirm the test results. The instant inventors have found very good correspondence when the test is completed on two separate devices on the same sample. Clearly, those of ordinary skill in the art will recognize that the foregoing is just one example of the many different ways embodiments of the instant invention could be implemented.

Table 1 below summarizes the steps involved in the specific example given above. It should be noted that, in some embodiments, additional fluid may need to be added to the bottom chamber when the pressure is released in step 14. As has been stated previously, the following series of steps has been offered only to aid in the understanding of the instant invention and not out of any intent to limit the practice of the invention to these specific pressures, times, and number of steps.

TABLE 1

Summary of a particular embodiment of the SAM test method.

| Step | Action |
| --- | --- |
| 1 | Place concrete in bottom chamber per ASTM C231 |
| 2 | Securely place lid |
| 3 | Add fluid through petcocks |
| 4 | Pressurize top chamber to 14.5 ± 0.1 psi |
| 5 | Press lever and record equilibrium pressure, $P_{2a}$ |
| 6 | Pressurize top chamber to 30 ± 0.1 psi |
| 7 | Press lever and record equilibrium pressure, $P_{2b}$ |
| 8 | Pressurize top chamber to 45 ± 0.1 psi |
| 9 | Press lever and record equilibrium pressure, $P_{2c}$ |
| 10 | Pressurize top chamber to 60 ± 0.1 psi |
| 11 | Press lever and record equilibrium pressure, $P_{2d}$ |
| 12 | Pressurize top chamber to 75 ± 0.1 psi |
| 13 | Press lever and record equilibrium pressure, $P_{2e}$ |
| 14 | Return pressure in bottom chamber and top chamber back to atmospheric pressure. |
| 15 | Repeat 3 thru 14 an additional time for equilibrium pressures $P_{2f}$ thru $P_{2j}$ |

Figure 2:
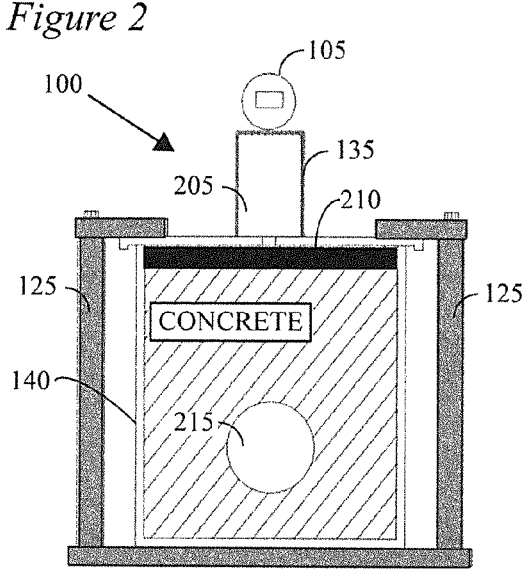
FIG. 2 illustrates an embodiment with concrete in place and reading for initiating a test.

Turning now to a description of how the equilibrium pressures obtained above might be used to provide an estimate of the air void quality in the tested concrete and how such might be related to the commonly used spacing factor, it has been determined that the difference in equilibrium pressures between an initial pressurization run and a subsequent run is related to the air void distribution. Note that, in some sense, the equilibrium pressure is an indirect measurement of the volume of the concrete in the chamber after compression. For example, consider the example of FIGS. 2 and 3. FIG. 2 contains a schematic diagram of the embodiment discussed above after the upper chamber 135 has been pressurized with air 205 but before it has been placed into fluid communication with the lower chamber 140. As can be seen, in the lower chamber 140 there is some amount of water 210. The air void distribution before exposure to the pressurized air is schematically illustrated by the bubble 215.

Figure 3:
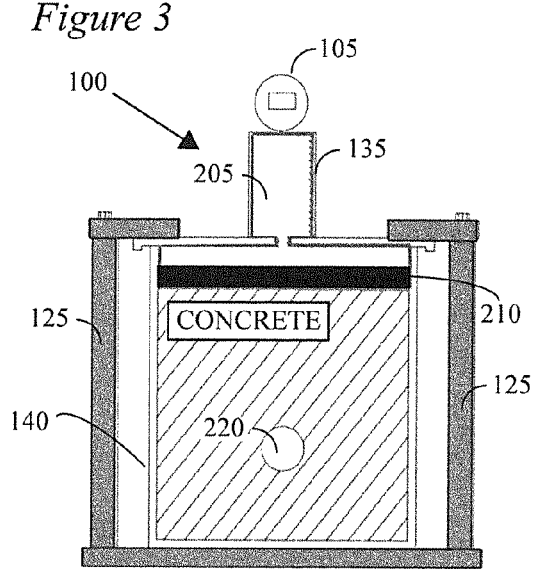
FIG. 3 contains a schematic illustration of the embodiment of FIG. 2 after the system has been equalized.

FIG. 3 illustrates conceptually the appearance of the lower chamber 140 after it has been placed in fluid communication with the upper chamber 135. As can be seen, the volume of water 210 remains unchanged because in this embodiment an incompressible fluid was used. However, the volume of air 205 has expanded, thereby compressing the concrete. As is shown schematically, in this example the representative bubble 215 has decreased in size (volume) in response to the increased pressure.

Notice, in this embodiment, that the equilibrium pressure is actually a surrogate for the change in the volume of the concrete. Said another way, the measured equilibrium pressure released into fluid communication from a known volume is indirectly representative of the resulting volume of the concrete after compression. If there is very little change in the equilibrium pressure when compared to the applied pressure then there is little volume change. If there is a significant drop in pressure then there is significant volume change. As such, it should be broadly understood herein that when an equilibrium pressure is mentioned, such could readily be expressed in terms of the volume of the compressed concrete instead.

According to an embodiment of the invention, the SAM number is defined to be the value of the difference between a first-run 580 equilibrium pressure and a second run 590 equilibrium pressure, multiplied by a constant:

$$\text{SAM Number} = (P_{EQ2} - P_{EQ1}) * C,$$

where "$P_{EQ1}$" and "$P_{EQ2}$" are the equilibrium pressures from different pressure runs, and "C" is the constant that may depend, among others, on the pressures that are used.

Figure 5:
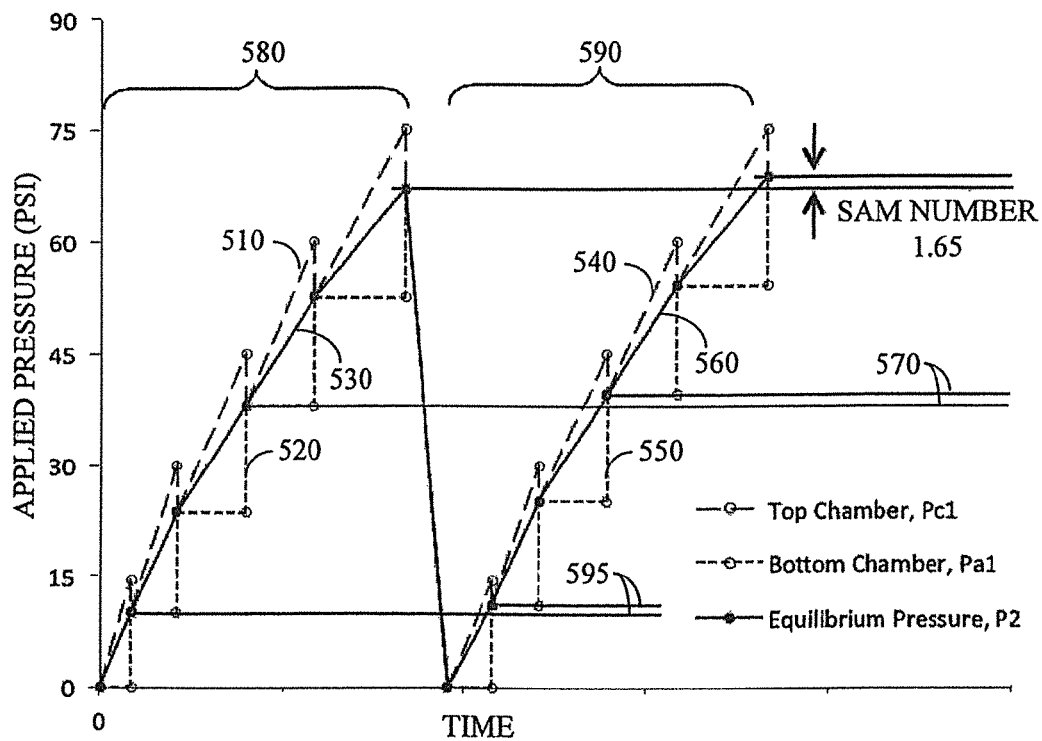
FIG. 5 contains an embodiment of pressure stages of one SAM test.

FIG. 5 provides a schematic illustration of how this might operate in practice. In the example presented by this figure, there are two pressure runs 580 and 590 of the sort described above. Each run involves initial upper chamber pressures 135 of 14.5, 30, 45, 60 and 75 psi. Curves 510 and 540 illustrate this for the first 580 and second 590 runs respectively.

Curves 520 and 550 illustrate the pressure in the lower chamber 140 before it is placed in fluid communication with the upper chamber 135 for the first 580 and second 590 runs respectively. Finally, curves 530 and 560 illustrate a sequence of equilibrium pressures for each of the two runs.

Of most importance for this graph is the equilibrium pressure differential labeled as "SAM Number" which, for this particular sample, is given to be 1.65 psi. It has been determined, based on the samples used and the tests run to date, that the C for this particular sample is 1.0. Thus, the SAM Number is equal to the pressure differential between equilibrium pressures obtained using the same initial top chamber pressures during the first and a subsequent run. Those of ordinary skill in the art will recognize that the value of C will likely need to be determined empirically.

Note that, in FIG. 5 the SAM Number could have been calculated much earlier in the process (e.g., the difference between the equilibrium pressures obtained from an initial upper chamber pressure of 45 psi 570) and comparable results would have been obtained. In brief, all that would be required in this embodiment is that at least two pressure runs be conducted, each of which produces at least one equilibrium pressure that are performed sequentially on the same concrete sample. Although the pressure differentials at high initial/equilibrium pressures are generally preferred, even relatively low pressures (e.g., differential 595 at 14.5 psi) could be useful, although with initial pressures different from the 75 psi initial pressure used in this example the value of C might be different from 1.0 and need to be recalculated.

As further discussion of the foregoing, suppose for purposes of illustration only, a five stage test is conducted that only involves two pressure runs 580 and 590 as is generally indicated in FIG. 5. Let P11 be the equilibrium pressure after the top chamber 135 has been opened to the bottom chamber 140 during the first stage (e.g., 14.5 psi initial pressure in FIG. 5) and let P1n be the equilibrium pressure during the nth stage, first run 580, with n=2, N. In the example of FIG. 5, N=5, and P1n, n=2, 5, would be the equilibrium pressures obtained during the first run from initial pressures of 30 psi, 45 psi, 60 psi, and 75 psi respectively.

Similarly, let P21 be the equilibrium pressure at the first stage of the second run 590 (i.e., with initial pressure equal to 14.5 psi in FIG. 5), with P2n being the equilibrium pressures at the subsequent stages, n=2,5 and initial pressures the same as before. As has been discussed previously, one numerical value that is useful for purposes of the instant embodiment is the difference $\Delta P = P15 - P25$ or, more generally, $\Delta Pk = P1k - P2k$, where k≥1.

It should be noted that in addition to $\Delta P5$ or any single $\Delta Pk$, combinations of corresponding equilibrium pressures from other runs (e.g., run 1 versus run 3, run 2 versus run 4, etc.) might give further information. Similarly, linear or other functional combination (e.g., quadratic, cubic, etc.) of the equilibrium pressure differences might be useful in some variations, e.g., a linear combination of the $\Delta Pk$'s might provide a more accurate estimate than any single $\Delta Pk$. Those of ordinary skill in the art will be able to devise methods of utilizing the $\Delta Pk$'s to determine the air void distribution.

Figure 4:
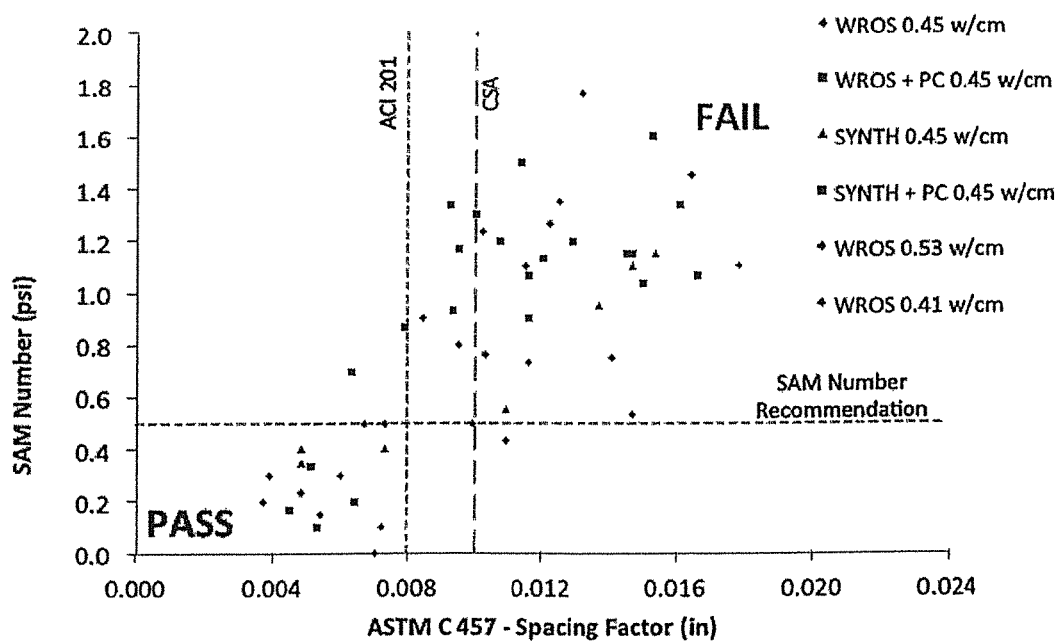
FIG. 4 contains experimental data that illustrate one possible relationship between SAM Number and Spacing Factor.

Turning next to FIG. 4 which contains experimental results obtained via the method set out above, as is indicated in this figure SAM Numbers less than 0.5 are broadly indicative of spacing factors less than 0.008. Said another way, where the SAM Number was less than 0.5 the corresponding spacing factor was less than 0.008 which testing has shown is sufficient to resist frost damage.

Note that it would also be possible to practice the methods taught herein at much higher pressures than 75 psi. This value was chosen because it was usable with the existing hardware and it provided a good correlation to spacing factor. Lower pressures (either at the beginning, ending, or an intermediate pressure or at the end) may also be used. Finally, the particular pressures, the number of such pressures, and the accuracy of the readings have all been suggested for purposes of illustration and not out of any intent to limit the invention to these particular embodiments. Selection of the particular pressures that are used, and the number of such pressures, the number of runs, etc., is something that is well within the ability of one of ordinary skill in the art and might need to be varied depending on the equipment used, the concrete being tested, etc.

Note further that, in some embodiments it will be possible to complete this test with a single chamber. This can be done by placing a known volume of concrete in a container and then directly or indirectly measuring the volume change from overpressure load that is applied to the concrete sample. This could done in many ways, but among them would be to add a fluid of known compressibility and volume above the concrete. This fluid may be water in some embodiments.

Then, as an overpressure load is applied, the concrete and fluid will compress. This volume change could be read by watching the level of the fluid drop with a site glass or fluid transducer (in the instance of a liquid) or read via a pressure meter (in the instance of a gas). Next the overpressure load will be reduced to a known value (in some instances it will be removed entirely) and then the load increased again to the same, or close to the same, overpressure value used previously. The volume change of the fluid and concrete from the second overpressure could then be compared to the previously obtained values from the first overpressure. The differences in these measurements will be indicative of the air void distribution in the concrete and will be relatable to the spacing factor, specific surface, or some other measurement of the air void distribution. Those of ordinary skill in the art will recognize that the over pressure load amounts that are used, as well as the exact method for measuring the volumetric change may need to be customized for different applications and such is well within the ability of one of ordinary skill in the art to devise.

Additionally it should be noted that although the instant disclosure discusses air voids in fresh concrete principally in terms of the spacing factor, obviously such could just as easily be represented in absolute terms, or in terms of any sort of arbitrary scale (e.g., "poor", "fair", "good", "better", etc.). Thus, when the terms "air void size distribution" are used in the specification and in the claims that follow, those terms should be broadly construed to cover instances where the determined air void quantity is reported in any sort of quantitative or qualitative manner.

Further, note that the particular pressures and accuracy of measurements mentioned herein were only given as examples and not out of any sort of attempt to limit the practice of the instant invention to those parameter values. Those of ordinary skill in the art will be able to readily determine alternative upper chamber initial pressures and accuracies that might be suitable for use in a given situation.

Still further, although water is suitable material which can be utilized in connection with the instant invention, it should be noted that other fluids (e.g., oil, air, inert gas, glycerol, or hydroxylated polymers, etc.) could be used instead as long as their compressibility is known for the temperature and pressures investigated. As the compressibility of these fluids increases then so would the pressures necessary to obtain a volume change of the concrete. Those of ordinary skill in the art would be able to readily determine alternative equilibrium pressures to compensate for the compressible fluid. However, since water is readily available, inexpensive, and largely incompressible it would be the preferred choice in most circumstances.

Even further, when the term air void distribution is used herein that term should be broadly interpreted to include, without limitation, the well-known spacing factor, specific surface, or any similar measure of the bubble content, spacing, etc., of air voids in concrete.

\* \* \*

Thus, the present invention is well adapted to carry out the objectives and attains the ends and advantages mentioned above as well as those inherent therein.

While the invention has been described and illustrated herein with reference to certain embodiments in relation to the accompanying drawings, various changes and further modifications may be made therein by those skilled in the art without departing from the spirit of the invention, the scope of which is determined from the appended claims.

What is claimed is:

1. A method of determining a parameter indicative of an air void distribution of a fresh concrete sample, wherein is provided a first and a second container configurable to be placed into fluid communication with each other, the method comprising:
   a. placing said fresh concrete sample in said first container;
   b. pressurizing said second container to a first pressure;
   c. placing said first container and said second container in fluid communication;
   d. determining a first equilibrium pressure;
   e. releasing at least a part of the pressure in the first container;
   f. removing said first and second container from fluid communication;
   g. pressurizing said second container to a second pressure;
   h. bringing said first container and said second container back into fluid communication with each other;
   i. determining a second equilibrium pressure; and,
   j. using at least said first equilibrium pressure and said second equilibrium pressure to determine said parameter indicative of said air void distribution of said fresh concrete sample.

2. The method of determining a parameter indicative of an air void distribution of a fresh concrete sample according to claim 1, wherein step (a) comprises the steps of:
   (a1) placing said fresh concrete sample in said first container, and,
   (a2) adding a fluid to said first container containing said fresh concrete until it is substantially full.

3. The method of determining a parameter indicative of an air void distribution of a fresh concrete sample according to claim 1, wherein said first pressure and said second pressure are approximately a same pressure.

4. The method of determining a parameter indicative of an air void distribution of a fresh concrete sample according to claim 3, wherein said first pressure and said second pressure are selected from the group consisting of 14.5 psi, 30 psi, 45 psi, 60 psi, and 75 psi.

5. The method of determining a parameter indicative of an air void distribution of a fresh concrete sample according to claim 1, further comprising the step of:
   k. using said parameter indicative of an air void distribution of said fresh concrete sample to estimate a value representative of a spacing factor of said fresh concrete sample.

6. The method determining a parameter indicative of an air void distribution of a fresh concrete sample according to claim 5, wherein said estimate of said air void distribution is obtained by subtracting said first equilibrium pressure from said second equilibrium pressure.

7. The method of determining a parameter indicative of an air void distribution of a fresh concrete sample according to claim 2, wherein said fluid is selected from the group consisting of water, oil, air, inert gas, glycerol, and hydoxylated polymers.

8. The method of determining a parameter indicative of an air void distribution of a fresh concrete sample according to claim 2, wherein said fluid is incompressible.

9. The method of determining a parameter indicative of an air void distribution of a fresh concrete sample according to claim 5, wherein step (k) comprises the steps of:
   (k1) using at least said first equilibrium pressure and said second equilibrium pressure to determine an estimate of a spacing factor for said fresh concrete sample, thereby determining said parameter indicative of said air void distribution of said fresh concrete sample.

10. The method of determining a parameter indicative of an air void distribution of a fresh concrete sample according to claim 1, wherein step (f) comprising the step of:
   (f1) completely releasing the pressure in said first container, thereby causing the pressure within said first container to at least approximately equal an atmospheric pressure.

11. The method of determining a parameter indicative of an air void distribution of a fresh concrete sample, wherein is provided a first and a second container configurable to be placed into fluid communication with each other, the method comprising:
   a. placing said fresh concrete sample in said first container;
   b. pressurizing said second container to a predetermined pressure;
   c. placing said first container and said second container in fluid communication;
   d. determining an equilibrium pressure;
   e. performing steps (b) through (d) a plurality of different times at a plurality of different predetermined pressures, thereby obtaining a plurality of first equilibrium pressures;
   f. releasing at least a part of the equilibrium pressure in the first container;
   g. after step (f), performing steps (b) through (d) again for each of said plurality of different predetermined pressures, thereby obtaining a plurality of second equilibrium pressures;
   h. using at least one of said plurality of first equilibrium pressures and a corresponding at least one of said plurality of second equilibrium pressures to determine said parameter indicative of said air void distribution of said fresh concrete sample.

12. The method of determining a parameter indicative of an air void distribution of a fresh concrete sample according to claim 11, wherein step (a) comprises the steps of:
   (a1) placing said fresh concrete sample in said first container, and,
   (a2) adding a fluid to said first container containing said fresh concrete until it is substantially full.

13. The method of determining a parameter indicative of an air void distribution of a fresh concrete sample according to claim 11, wherein said plurality of predetermined pressures are selected from the group consisting of 14.5 psi, 30 psi, 45 psi, 60 psi, and 75 psi.

14. The method determining a parameter indicative of an air void distribution of a fresh concrete sample according to claim 11, further comprising the step of:
   i. using said parameter indicative of an air void distribution of said fresh concrete sample to estimate an air void distribution of said fresh concrete sample.

15. The method of determining a parameter indicative of an air void distribution of a fresh concrete sample according to claim 12, wherein said fluid is selected from the group consisting of water, oil, air, inert gas, glycerol, and hydoxylated polymers.

16. The method of determining a parameter indicative of an air void distribution of a fresh concrete sample according to claim 11, wherein step (f) comprising the step of:

(f1) completely releasing the pressure in said first container, thereby causing the pressure within said first container to at least approximately equal an atmospheric pressure.

\* \* \* \* \*